US011906472B2

(12) United States Patent
Jiang et al.

(10) Patent No.: US 11,906,472 B2
(45) Date of Patent: Feb. 20, 2024

(54) NON-DESTRUCTIVE CONCRETE STRESS EVALUATION

(71) Applicant: WiSys Technology Foundation, Inc., Madison, WI (US)

(72) Inventors: Hanwan Jiang, Platteville, WI (US); Hanyu Zhan, Las Cruces, NM (US); Ruinian Jiang, Las Cruces, NM (US)

(*) Notice: Subject to any disclaimer, the term of this patent is extended or adjusted under 35 U.S.C. 154(b) by 544 days.

(21) Appl. No.: 17/263,229

(22) PCT Filed: Jul. 29, 2019

(86) PCT No.: PCT/US2019/043943
§ 371 (c)(1),
(2) Date: Jan. 26, 2021

(87) PCT Pub. No.: WO2020/023967
PCT Pub. Date: Jan. 30, 2020

(65) Prior Publication Data
US 2021/0164945 A1    Jun. 3, 2021

Related U.S. Application Data

(60) Provisional application No. 62/716,530, filed on Aug. 9, 2018, provisional application No. 62/703,965, filed on Jul. 27, 2018.

(51) Int. Cl.
*G01N 29/50* (2006.01)
*G01L 1/22* (2006.01)
(Continued)

(52) U.S. Cl.
CPC ............ *G01N 29/50* (2013.01); *G01L 1/22* (2013.01); *G01N 29/07* (2013.01); *G01N 33/383* (2013.01);
(Continued)

(58) Field of Classification Search
CPC ...... G01N 29/50; G01N 29/07; G01N 33/383; G01N 2291/011; G01N 2291/0232;
(Continued)

(56) References Cited

U.S. PATENT DOCUMENTS 5,821,430 A    10/1998  Kwun et al.
6,591,681 B1    7/2003  Shimada et al.
(Continued)

FOREIGN PATENT DOCUMENTS

EP    0526855    2/1993

*Primary Examiner* — Tung S Lau
(74) *Attorney, Agent, or Firm* — Boyle Fredrickson S.C.

(57) ABSTRACT

A system of monitoring diffuse waves over a concrete beam under different loads. Ultrasound transmitters and receivers are placed over the concrete beam to emit sound waves and collect diffuse waves under different loads. The waveform variations are observed to quantify a decorrelation coefficient (DC) indicating global structural changes and crack position. An inversion of the correlations is applied to estimate distribution density at each localized position following the sensitivity kernel and inversion algorithms. Then, three-dimensional imaging comprised of density values at each localized position are generated to indicate number, position, and depth of multiple cracks.

18 Claims, 3 Drawing Sheets

(51) Int. Cl.
*G01N 29/07* (2006.01)
*G01N 33/38* (2006.01)

(52) U.S. Cl.
CPC ............... *G01N 2291/011* (2013.01); *G01N 2291/0232* (2013.01); *G01N 2291/0289* (2013.01); *G01N 2291/105* (2013.01)

(58) Field of Classification Search
CPC ..... G01N 2291/0289; G01N 2291/105; G01N 2291/103; G01N 29/043; G01L 1/22
See application file for complete search history.

(56) References Cited

U.S. PATENT DOCUMENTS

| | | | | |
|---|---|---|---|---|
| 7,107,851 | B2* | 9/2006 | Owen | G01N 29/449 |
| | | | | 702/54 |
| 7,894,303 | B2* | 2/2011 | Tsurugaya | G01S 7/52004 |
| | | | | 367/138 |
| 8,594,350 | B2* | 11/2013 | Hooley | H04S 7/301 |
| | | | | 381/59 |
| 9,448,100 | B2* | 9/2016 | Nagae | A61B 8/14 |
| 2003/0098697 | A1 | 5/2003 | Tanaka | |
| 2010/0312496 | A1* | 12/2010 | Armitage | G01N 29/348 |
| | | | | 73/602 |
| 2013/0220017 | A1 | 8/2013 | Kim et al. | |
| 2013/0338944 | A1* | 12/2013 | Nagae | G01H 1/00 |
| | | | | 702/56 |
| 2014/0321760 | A1* | 10/2014 | Oishi | A61B 5/7203 |
| | | | | 382/218 |
| 2018/0156728 | A1* | 6/2018 | Pourkazemi | G01N 22/00 |

* cited by examiner

NON-DESTRUCTIVE CONCRETE STRESS EVALUATION

CROSS REFERENCE TO RELATED APPLICATION

This application claims the benefit of U.S. Provisional Application No. 62/703,965 filed Jul. 27, 2018 and U.S. Provisional Application No. 62/716,530 filed Aug. 9, 2018, both of which are hereby incorporated by reference in their entireties.

BACKGROUND OF THE INVENTION

The present invention relates generally to detection of defects in concrete structures and in particular to a nondestructive technique for evaluating cracks and stress distributions within concrete.

Concrete is a multiple composite material made of sand grains, aggregate stones, steel bars, and pores. Due to the brittle nature of concrete, structural deficiencies caused by cyclic loading and corrosions are typically initiated by internal cracking which may lead to further structural failures. The majority of bridges constructed in the United States are made of concrete. Many of them are structurally deficient or approaching their design lifecycle.

The use of waves, including ultrasound and optic waves, are useful tools for the detection of internal changes and perturbations within materials and are generally better than visual inspection alone. By observing the behavior of direct waves through materials, small amounts of energy scattering within the material can indicate the existence of internal cracks. While these techniques may be used for many materials, they are not useful in measuring cracks in concrete.

The heterogeneous nature of concrete causes strong scattering behaviors during wave propagations. As a result, waves lose their initial propagation directions rapidly and follow very complex trajectories that become mostly diffuse within the medium. In addition, micro defects in concrete usually develop at length scales that are too small for detection by low-frequency waveforms. Thus detection techniques that work with direct waves and single reflection patterns are difficult to utilize for heterogeneous concrete materials.

Known approaches utilizing direct waves or singly reflected detection in concrete have attempted to overcome these challenges by avoiding high frequency ranges that cause high levels of scattering or have tried to filter out the scattering effects. However, these methods are not suitable for evaluating deeper cracks or the existence of micro-cracks that cannot be easily seen.

SUMMARY OF THE INVENTION

Diffuse waves, sometimes called coda waves, denote the trailing parts of the initial wave that experience the multiple scattering behaviors and are measured beyond the direct propagating part of the wave. The present inventors have found that diffuse waves observed at a specific location represent the superposition of abundant partial waves following different trajectories over a large volume and carry important information that can reveal weak perturbations caused by distortions in the media.

The present inventors have also found that diffuse waves have much longer traveling paths and traverse and change directions repeatedly as compared to direct waves. Thus these diffuse waves provide large detection volumes and greater sensitivity to concrete perturbations.

The present invention provides a system of monitoring diffuse waves over a concrete beam under different loads. Ultrasound transmitters and receivers are placed over the concrete beam to emit sound waves and collect diffuse waves under different loads. The waveform variations are observed to quantify a decorrelation coefficient (DC) indicating global structural changes and crack position. An inversion of the correlations is applied to estimate distribution density at each localized position following the sensitivity kernel and inversion algorithms. Then, three-dimensional imaging comprised of density values at each localized position are generated to indicate number, position, and depth of multiple micro-cracks.

In one embodiment, the present invention provides a testing system for concrete structures including a load sensor positionable to measure a load on the concrete structure to distinguish between at least two different load values; a plurality of transmitters positionable on the structure and configured to independently transmit acoustic excitation waves into the structure; a plurality of receivers positionable on the structure and configured to receive diffuse waves of the excitation waves from the plurality of transmitters; and an electronic computer executing a program stored in a non-transitory medium to: receive the diffuse waves from the plurality of receivers; calculate a decorrelation coefficient based on the diffuse waves and a wave speed of the diffuse waves for at least two different load values; calculate a sensitivity kernel based on the diffuse waves; apply an inversion algorithm to estimate a distribution density based on the decorrelation coefficient and the sensitivity kernel and indicating the presence of defects within the beam.

It is thus a feature of at least one embodiment of the invention to utilize diffuse waves, instead of direct waves, in evaluating defects in concrete where the superposition of multiple waves carry important information lost in direct waves or singly reflected wave detection due to the heterogeneous nature of concrete.

The defects may be cracks.

It is thus a feature of at least one embodiment of the invention to identify scattering behaviors caused by cracks and other small defects in the concrete material.

The electronic computer may further execute the program stored in the non-transitory medium to receive multiple diffuse waves at multiple times at each load value and calculate a mean diffuse wave from the multiple diffuses wave.

It is thus a feature of at least one embodiment of the invention to eliminate deviations in received waves caused by noise not caused by the scattering behavior of the defects.

The electronic computer may further execute the program stored in the non-transitory medium to output an image of the distribution density as a function of beam location.

It is thus a feature of at least one embodiment of the invention to provide a quick visual indication of defect location within the three-dimensional model relating to an actual position within the concrete material.

The electronic computer may further execute the program stored in the non-transitory medium to calculate a depth of the micro-cracks within the beam.

It is thus a feature of at least one embodiment of the invention to estimate other defect information to a high accuracy even though the defects cannot be visually seen.

The excitation waves may be transmitted at a frequency between 100 kHz and 200 kHz. The excitation waves may be transmitted at a frequency of 150 kHz.

It is thus a feature of at least one embodiment of the invention to provide a balance between high sensitivity to diffuse wave detection and low attenuation due to the scattering behavior of waves.

The load sensor may be a strain gauge. The load sensor may be a load jack.

It is thus a feature of at least one embodiment of the invention to measure strains on the beam, whether provided naturally or artificially, to anticipate stress conditions of the beam before cracks form.

The plurality of transmitters may be positioned along a horizontal centerline of the beam, the centerline extending along the axis of the beam and centered between a width of the beam.

It is thus a feature of at least one embodiment of the invention to emit wave propagation through the entire beam volume.

The plurality of receivers may extend along the axis of the beam and flank the centerline of the beam to surround the plurality of the transmitters. A second plurality of receivers may be positioned on a perpendicular surface to the plurality of receivers.

It is thus a feature of at least one embodiment of the invention to provide a large wave detection volume in three dimensions.

The diffusion coefficient may be estimated using nonlinear least-squares or genetic algorithms.

It is thus a feature of at least one embodiment of the invention to significantly simplify the data processing using a general approach which may be processed in real-time. The decorrelation coefficient may be calculated using the following equation:

$$DC^l(t, \varepsilon, r_{i,j}) = 1 - \frac{\int_0^t \langle E^l[r_{i,j}, t'(1-\varepsilon)]\rangle\langle E^{l-1}(r_{i,j}, t')\rangle dt'}{\sqrt{\int_0^t \langle E^l[r_{i,j}, t'(1-\varepsilon)]\rangle^2 dt' \int_0^t \langle E^{l-1}(r_{i,j}, t')\rangle^2 dt'}}$$

where t indicates the wave propagation time, $r_i$, $r$ and $r_j$ represent the central positions of the associated elementary cells of the beam, l denotes the loading step, E represents a reference diffuse wave, $\varepsilon$ is the relative velocity variations between two diffuse waves.

The sensitivity kernel may be calculated using the following equation:

$$K^l(r_i, r, r_j, t) = \frac{|r_i - r| + |r_j - r|}{4\pi D^l(r_{i,j})|r_i - r||r_j - r|} \exp\left[\frac{(r_{ij})^2 - (|r_i - r| + |r_j - r|)^2}{4D^l(r_{i,j})t}\right]$$

where t indicates the wave propagation time, $r_i$, $r$ and $r_j$ represent the central positions of the associated elementary cells of the beam, D denotes the diffusion coefficient.

These particular objects and advantages may apply to only some embodiments falling within the claims and thus do not define the scope of the invention.

DETAILED DESCRIPTION OF THE PREFERRED EMBODIMENT

Figure 1:
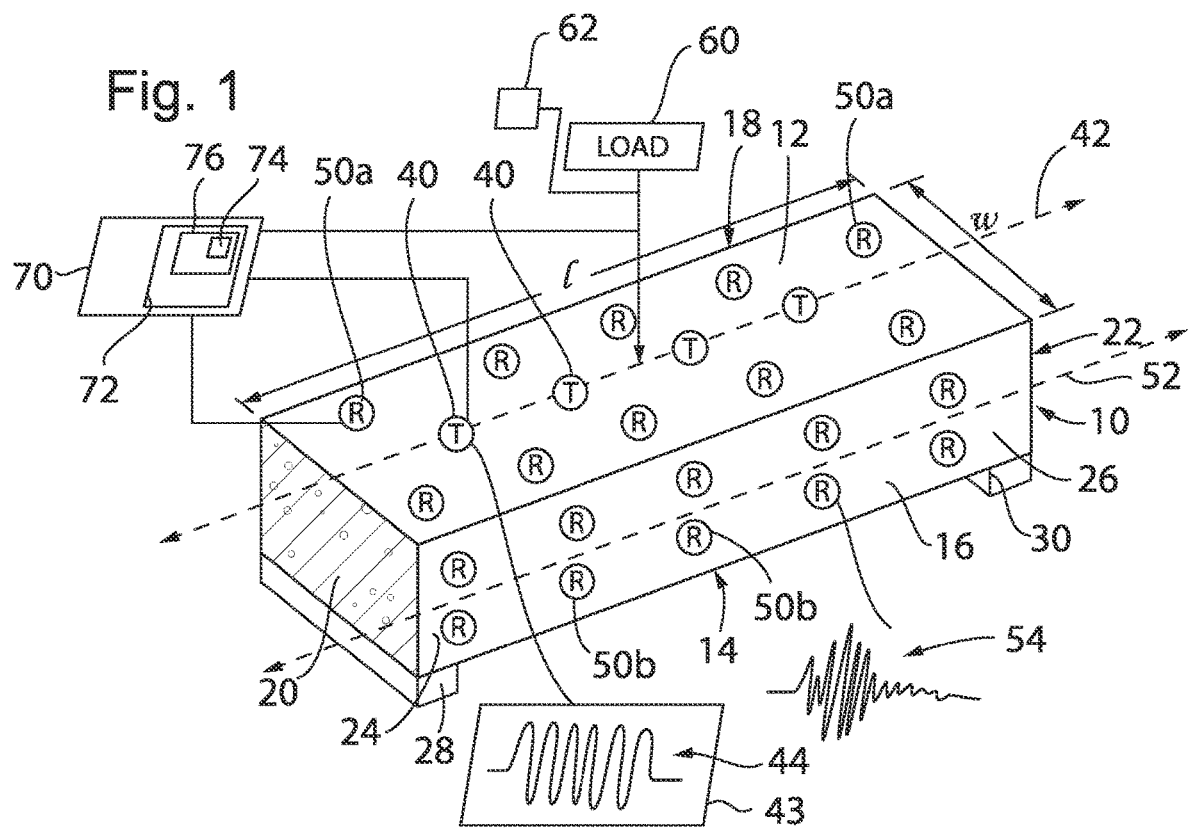
FIG. 1 is a perspective view of a micro-crack detection system of the present invention for use with a solid concrete beam suspended over the ground at opposed bearing points.

Referring now to FIG. 1, a concrete beam 10 is defined by a solid concrete block having an upper surface or deck 12, for example, integral with the concrete beam 10, supporting weight thereon and opposite a lower surface 14. The block has outer side surfaces formed by front and back surfaces 16, 18 extending along a length of the concrete beam 10 and left and right surfaces 20, 22 extending along a width of the concrete beam 10. In one embodiment of the present invention, the block of the concrete beam 10 may comprise of a solid volume having at least the following dimensions: 596 cm by 87 cm by 30 cm. It is understood that the concrete beam 10 may take many different dimensions in accordance with the present invention.

The outer, opposed ends 24, 26 of the length of the concrete beam 10 may be supported on bridge bearings 28, 30, respectively, connecting the concrete beam 10 to vertical supports extending upwardly from the ground (not shown), for example, supported on top of bridge piers, bridge abutments, or other vertical load bearing members. The concrete beam 10 may be generally form part of a bridge structure extending above and generally parallel to the ground and desirably spanning over physical obstacles such as water, a valley, a road and the like without obstructing passage underneath.

A plurality of frequency transmitters 40 may be installed on the deck 12 of the concrete beam 10 spaced along the length of the concrete beam 10, and may be centered along a centerline 42 between the front and back surfaces 16, 18 of the concrete beam 10. In one embodiment of the present invention the plurality of transmitters 40 includes four frequency transmitters 40 spaced evenly along the length of the concrete beam 10 on the centerline 42. The plurality of frequency transmitters 40 may be attached to the deck 12 using a temperature and chemically resistant adhesive such as high vacuum silicone grease.

Each of the frequency transmitters 40 may be connected to an ultrasound generator 43, for example a high-power ultrasonic system commercially available under the trade name "RAM-5000" produced by RITEC Inc. of Warwick, RI, to generate an ultrasound impulse 44. The ultrasound impulse 44 may be a single frequency excitation signal. The ultrasound impulse 44 may have a frequency ranging between 60 kHz to 400 kHz, and between 100 kHz and 200 kHz, and preferably centered on 150 kHz, and may be driven by a voltage ranging between 3 to 9 V and preferably centered on 5.7 V. The excitation period T may last between several minutes to several hours. The ultrasound impulse 44 may be controlled by a processor as further described below.

The preferred frequency presents a compromise between the detection ability and sensitivity of the waves. For example, high frequencies corresponding to short waves are more sensitive to small-scale medium changes but intensify wave energy attenuation due to scattering and dissipation behaviors. Low frequencies corresponding to long waves are less sensitive to small-scale medium changes but reduce wave energy attenuation for greater detection ability.

The frequency transmitters 40 are used in conjunction with receivers 50 disposed on an outer surface of the concrete beam 10 around the frequency transmitters. The receivers 50 are able to sample wave signals 54 consistent with the excitation frequency of the frequency transmitters 40, and may sample signals at frequencies satisfying the Nyquist rate. Each of the receivers 50 may communicate with a processor to store and process the received wave signals 54 as further described below.

A first set of receivers 50a may be installed on the deck 12 along the length of the concrete beam 10. In one embodiment of the present invention, the first set of receivers 50a are spaced evenly in two rows on the deck 12 toward a front and back of the deck 12 respectively and flanking the centerline 42 of the deck 12 between the front and back surfaces 16, 18. The first set of receivers 50a may include ten receivers having a first row of five receivers extending along a front of the deck 12 and a second row of five receivers extending along a back of the deck 12.

A second set of receivers 50b may be installed on the front surface 16 of the concrete beam 10. In one embodiment of the present invention, the second set of receivers 50b are spaced evenly in two rows on the front surface 16 toward a top and bottom of the front surface 16 respectively and flanking a centerline 52 of the front surface 16 between the deck 12 and lower surface 14. The second set of receivers 50b may include ten receivers having a first row of five receivers extending along a top of the front surface 16 and a second row of five receivers extending along a bottom of the front surface 16. Alternatively, or in addition, the second set of receivers 50b may be installed on the back surface 18 in a similar manner as described with respect to the front surface 16.

The first and second set of receivers 50a, 50b may be attached to the deck 12 using a temperature and chemically resistant adhesive such as high vacuum silicone grease.

Although the frequency transmitters 40 and first and second set of receivers 50a, 50b are shown distributed uniformly across the entire outer surface of the concrete beam 10, the frequency transmitters 40 and first and second set of receivers 50a, 50b may be installed only at desired portions of the concrete beam 10 where crack evaluation is desired, for example, only on one longitudinal side of the concrete beam 10.

It is understood that the receivers 50 are positioned to surround the frequency transmitters 40 in order to detect diffuse wave signals 54 flowing through the concrete beam 10 as emitted by the frequency transmitters 40. It is desired that a distance between each transmitter-receiver pair is between 20 cm and 1 m, and desirably more than 20 cm but less than 40 cm where the receivers are far enough so that frequency waves experience scattering effects but close enough so that the received signal is strong enough to be detected. High-power amplifiers may be used to allow for greater distances between each transmitter-receiver pair.

In one embodiment, the frequency transmitters 40 and receivers 50 may be transducers having both the ability to act as signal emitters and signal receivers. Therefore certain transducers may be configured to act as signal emitters at certain times and some transducers may be configured to act as signal receivers at certain times. In this respect, the transducers can be quickly switched between signal emitter and receiver for greater detection flexibility.

An external load 60 may be applied to the concrete beam 10 thus inducing an interior stress variation within the concrete beam 10. The external load 60 may be applied naturally, for example, by a weight of vehicles or pedestrians passing over the concrete beam 10 in the normal course of use of the bridge, or may be artificially applied by a hydraulic load jack placed toward the center of the concrete beam 10 to exert a predetermined and controlled force on the concrete beam 10. The external load 60 may generally vary between 0 kN and 130 kN.

The external load 60 may be measured by a load sensor 62. In one embodiment of the present invention the load sensor 62 may be a strain gauge measuring at least one of a force, pressure, tension, weight, etc. applied by the external load 60. In another embodiment of the present invention, the load sensor 62 may be the hydraulic load jack applying a known load onto the concrete beam 10.

Figure 2:
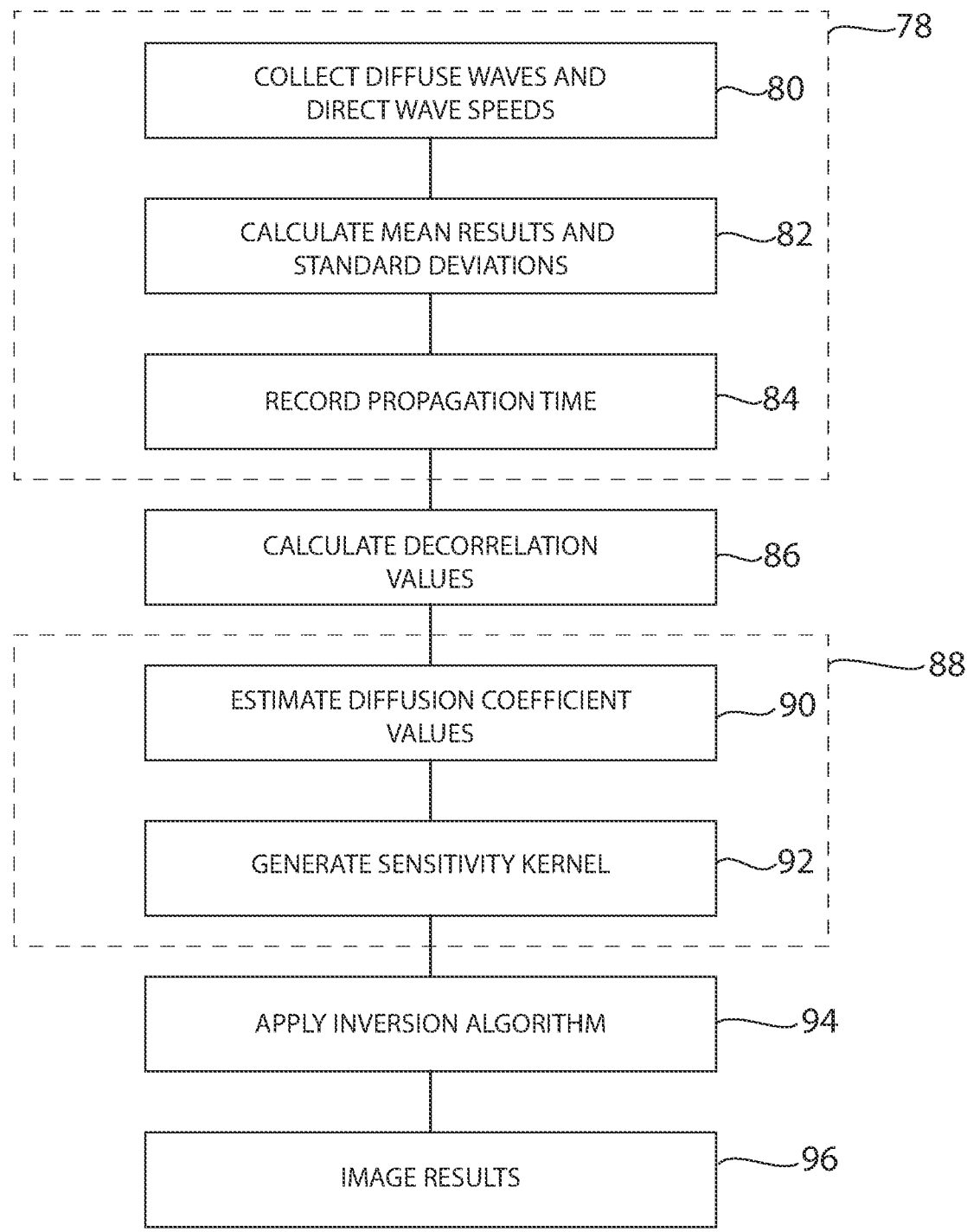
FIG. 2 is a flow chart showing a method of detecting cracks within concrete.

Referring to FIG. 2, the assembly described above may be used to collect diffuse wave signals 54 under different loads in order to estimate and image crack location and crack depth. The assembly may also be used to estimate an image stress changes in absolute stress values within the concrete beam 10.

In one embodiment of the present invention a method of evaluating defects may include the following steps: 1) observing diffuse wave variations under different loads, 2) calculating the decorrelation (DC) values, 3) estimating diffusion coefficient values and generating sensitivity kernels, and 4) applying the inversion algorithm to generate a three-dimensional image based on estimated density values in each local position. Thus a position and depth of microcracks may be determined with a high degree of accuracy.

Specifically, these steps are executed using the methods and models described in further detail below with respect to the following embodiments.

Embodiment 1

1) Collection of Diffuse Ultrasound Measurements

Referring still to FIG. 2, and according to one embodiment of the present invention, diffuse wave observation steps 78 may be carried out by applying various external loads 60 to the concrete beam 10 at desired intervals as predetermined by the user, for example, by using a hydraulic load jack. In one embodiment of the present invention, the external load 60 may be increased from 0 kN to 130 kN at 10 kN increments and then decreased back to 0 kN at 20 kN increments. The external load 60 may be held for at least five minutes to stabilize building conditions before changing to a different load value.

At each external load 60 interval, the plurality of frequency transmitters 40 may generate an ultrasound impulse 44, for example, having an amplitude $E_0=\pm 5.7$ V at frequency $f_c=150$ kHz. $E_0$ is related to the initial energy generated by the transmitter at position r=0 at t=0. Each of the receivers 50 may receive weight signals within the range of the ultrasound impulse 44, for example, receiving at 3 MHz frequency.

An electronic computer 70 including a processor 72 executing a program 74 stored in non-transitory memory 76 may coordinate the operation of the above-described components. For example, the processor 72 may control or trigger the emission of ultrasound impulse 44 from the plurality of frequency transmitters 40. The processor 72 may also receive and store in memory 76 the received diffuse wave signals 54 $<E^i(r_{i,j}, t)>$ where t indicates a wave propagation time and $r_{ij}$ indicates the distance between the transmitter 40 and the receiver 50 as indicated by process block 80.

The ultrasound impulse 44 is repeated, for example, between 50 to 100 times, and the mean results $<E^i(r_{i,j}, t)>$ from each receiver 50 are calculated to decrease deviations caused by measurement noises, and the standard deviation values are utilized to estimate the noise levels as indicated by process block 82.

Each transmitter 40 and receiver 50 pair may have an independent trigger and time counter to record the propagation time t accurately as indicated by process block 84.

The data received from the transmitters 40 and receivers 50 may be stored in the non-transitory memory 76 and may be further processed by the processor 72 as further described below.

2) Diffusion Equation and Coda Wave Interferometry Model Development:

Diffuse wave propagation is similar to heat diffusion (i.e., random work process) and it in space and time statistically follows the diffusion equation, $$D\Delta\langle E(r,t)\rangle - \frac{\partial\langle E(r,t)\rangle}{\partial t} - a\langle E(r,t)\rangle = E_0\delta(t)\delta(r) \quad (1)$$

where $\Delta$ and $\delta$ are Laplacian operator and Dirac delta function, respectively. $E_0$ denotes the initial energy deposited at position r=0 at time t=0 and $\langle E(r, t)\rangle$ is the mean energy density value (energy per area) at position r at propagation time t. D denotes the diffusion coefficient with dimension length squared per time and a is the dissipation coefficient with dimension inversion time.

The high degree of homogeneities and heterogeneities in large concrete structures cause D and $\sigma$ to be varied with positions and loads. In addition, the beam is large enough that diffuse wave reflections at the boundaries are weak; thus, the diffuse wave signal observations $\langle E^l(r_{i,j}, t)\rangle$ now are approximately modeled by the three-dimensional solution of the diffusion equation, $$\langle E^l(r_{i,j},t)\rangle = \frac{E_0}{[4\pi D^l(r_{i,j})t]^{3/2}}\exp\left[\frac{-r_{ij}^2}{4D^l(r_{i,j})t} - a^l(r_{i,j})t\right] \quad (2)$$

and $$p^l(r_{i,j},t) = \frac{\langle E^l(r_{i,j},t)\rangle}{E_0} = \frac{1}{[4\pi D^l(r_{i,j})t]^{3/2}}\exp\left[\frac{-r_{ij}^2}{4D^l(r_{i,j})t} - a^l(r_{i,j})t\right] \quad (3)$$

where $E_0$ is the excitation impulse in the experiments. Recall that is the distance between the source $S_i$ and the receiver $R_j$, and the subscript l denotes the loading step. $D^l(r_{i,j})$ and $a^l(r_{i,j})$ are the associated diffusion and dissipation coefficients. The normalized impulse response $P^l(r_{i,j}, t)$ in Eq. (3), sometimes called diffusion envelop, denotes the probability density function of the diffuse energy transportation. In finite media, the reflections at boundaries should be considered, and then the diffusion solution is the sum of the infinite medium solutions corresponding to different mirror images of the source.

In strongly scattering media, loads below structural serviceability stage will slightly stretch or squeeze the medium size, which further cause the tension or compression effects of diffuse waveforms; whereas defects such as micro-cracks worked as extra scatters will cause waveform distortions. Diffuse waves are sometimes called coda wave in geophysics, and Coda Wave Interferometry (CWI) is a straightforward and effective method to calculate diffuse wave decorrelations (DC) induced by medium defects. It is expressed as, $$DC(T,T_w,\varepsilon) = 1 - CC(T,T_w,\varepsilon) = \\ 1 - \frac{\int_{T-T_w}^{T+T_w}\langle E'[r,t'(1-\varepsilon)]\rangle\langle E(r,t')\rangle dt'}{\sqrt{\int_{T-T_w}^{T+T_w}\langle E'[r,t'(1-\varepsilon)]\rangle^2 dt'\int_{T-T_w}^{T+T_w}\langle E(r,t')\rangle^2 dt'}} \quad (4)$$

where E represents a reference diffuse wave and E' denotes a diffuse wave to be inspected. T denotes the center of a time window of length $2T_w$. $\varepsilon$ is the relative velocity variations between two diffuse waves and its value is determined by maximizing the correlation coefficient (CC) values; or in other words, making the inspected wave best resemble the reference wave. The parameter $\varepsilon$ is utilized to filter out waveform changes due to stress changes. Specifically, if only weak stress changes exist, by varying E values the tension or compression effects between two diffuse waves should be removed and the DC values should be pretty small; however, defects causing waveform distortion will significantly increase decorrelation (DC) values.

Instead of using time windows to select specific parts of diffuse waves, directly calculate the decorrelation coefficients of diffuse wave observations during the whole propagation time t for each source-receiver pair between every two successive loading steps. These calculations significantly simplify the data processing and demonstrate the generality of the approach. Eq. (4) now is written by $$DC^l(t,\varepsilon,r_{i,j}) = 1 - \frac{\int_0^t\langle E^l[r_{i,j},t'(1-\varepsilon)]\rangle\langle E^{l-1}(r_{i,j},t')\rangle dt'}{\sqrt{\int_0^t\langle E^l[r_{i,j},t'(1-\varepsilon)]\rangle^2 dt'\int_0^t\langle E^{l-1}(r,t')\rangle^2 dt'}} \quad (5)$$

Applying the Model:

The decorrelation coefficient $DC^l(t, \varepsilon, r_{i,j})$ may be calculated between every two successive loading steps using Eq. (4) above as indicated by process block 86.

3) Sensitivity Kernel Model Development:

A wave generated by source $S_i$ at position $r_i=(x_i, y_i, z_i)$ at time t=0, visits a volume dv at position r=(x, y, z) at time t', and is collected by receiver $R_j$ at position $r_j=(x_j, y_j, z_j)$ at propagation time t. The two paths, from $S_i$ to dv and from dv to $R_j$, are assumed to be independent. Then the associated probability is equal to the product of two probabilities: the probability of the wave propagates from $r_i$ to r in a time t', and the probability of the wave propagates from r to $r_j$ in a time t–t', $$P(r_i,r,r_j,t',t)=P(r_i,r,t')P(r,r_j,t-t') \quad (6)$$

Then the total probability of wave propagating from the source to the receiver in time t is the probability summation of all possible trajectories in the volume V, and it is given as, $$P(r_i,r_j,t)=\int_V P(r_i,r,r_j,t',t)dv(r)=\int_V P(r_i,r,t')P(r,r_j,t-t')dv(r) \quad (6)$$

If both sides of Eq. (7) is integrated over the interval $0 \leq t' \leq t$ and divided by $P(r_i, r_j, t)$, $$t=\int_V K(r_i,r,r_j,t)dv(r') \quad (8)$$

where $$K(r_i, r, r_j, t) = \frac{1}{P(r_i, r_j, t)} \int_0^t P(r_i, r, t') P(r, r_j, t-t') dt' \quad (9)$$

Here, $K(r_i, r, r_j, t)$ called the Sensitivity Kernel represents the time-of-flight (or probability) distribution of diffuse waves generated at position $r_i$, visiting location $r$ and detected at position $r_j$ at time $t$. For large-size strongly scattering media, substituting Eq. (3) into (9) with a few simplifications leads to the following expression for the three-dimensional Sensitivity Kernel expression, $$K^l(r_i, r, r_j, t) = \frac{|r_i - r| + |r_j - r|}{4\pi D^l(r_{i,j})|r_i - r||r_j - r|} \exp\left[\frac{(r_{ij})^2 - (|r_i - r| + |r_j - r|)^2}{4D^l(r_{i,j})t}\right] \quad (10)$$

Note that the derivations of Eqs. (6)-(10) do not include multiple reflections effects among different perturbations (e.g., micro-cracks). This is a reasonable initial assumption especially when the distances between perturbations are large compared to the wavelength.

Applying the Model:

The sensitivity kernel generations steps 88 may include estimating the values of the diffusion coefficient $D^l(r_{i,j})$ from the mean $<E^l(r_{i,j}, t)>$ results using nonlinear least-squares or genetic algorithms as indicated by process block 90. Then, the concrete beam is discretized into elementary cells of size $\delta V=3$ cm×3 cm×3 cm with cell number $N_c=199\times29\times10$, and the Sensitivity Kernel $K^l(r_i, r, r_j, t)$ is modeled with Eq. (10) above.

To generate the Sensitivity Kernel $K^l(r_i, r, r_j, t)$, first the values of $D^l(r_{i,j})$ and $a^l(r_{i,j})$ should be jointly estimated from the mean $<E^l(r_{i,j}, t)>$ results by applying nonlinear least-squares or genetic algorithms to Eq. (3) (or Eq. (2)). For estimating their values, two important requirements must be met: 1) the synthetic envelop by inserting their estimation values into Eq. (3) have the least square values with the associated $P^l(r_{i,j}, t)$ (or $<E^l(r_{i,j}, t)>$) measurement results, and 2) since peak-arriving time of diffuse waves carry important information of medium perturbations, the peak-arriving time of the synthetic envelops and measurement results must agree. The Sensitivity Kernel then can be generated with the estimated $D^l(r_{i,j})$ values through Eq. (10) as indicated by process block 92.

4) Three-Dimensional Imaging Results

Model Development:

The decorrelation coefficient (Eq. (4)) can be theoretically modeled using its density changes induced by each localized perturbation, and this relationship is given by $$DC^l(t, \varepsilon, r_{i,j}) = \oint \frac{c^l(r_{i,j}) \sigma^l(r)}{2} K^l(r_i, r, r_j, t) dV(r) \quad (11)$$

where $c^l(r_{i,j})$ denotes direct wave speed. The typical $c^l(r_{i,j})$ values of ultrasound wave propagated in concrete materials are on the order of several thousand meters per second, thus, stress variations and perturbations in the concrete beam only slightly changes the $c^l(r_{i,j})$ values. $\sigma^l(r')$ named the spatial density of the effective scattering cross-section, is a key parameter to evaluate each position $dV(r')$ contributed to the decorrelations. At each loading step, estimating $\sigma^l(r')$ values from $DC^l(t, \varepsilon, r_{i,j})$ calculations from all available source-receiver pairs measurements (i.e., $<E^l(r_{i,j}, t)>$) defines the inverse problem. For studying this problem, the concrete beam is discretized into elementary cells of size $\delta V$ with the total cells number $N_c$, and each cell is considered as a candidate position of the perturbations. Eq. (8) now is written by, $$DC^l(t, \varepsilon, r_{i,j}) = \quad (12)$$
$$\sum_1^{N_c} \frac{c^l(r_{i,j}) K^l(r_i, r, r_j, t) \delta V}{2} \sigma^l(r) = \sum_1^{N_c} G^l(r_i, r, r_j, t) \sigma^l(r)$$

Here, $r_i$, $r$ and $r_j$ represent the central positions of the associated elementary cells. $G^l(r_i, r, r_j, t)$ can be considered to be a weight function of $\sigma^l(r')$.

In general, the total cells number $N_c$ is much larger than the $DC^l(t, \varepsilon, r_{i,j})$ number $N_{DC}$, so Eq. (9) corresponds to an underdetermined equations system. For example, there are a total of 4 sources and 20 receivers to collect diffuse wave signals, which implies $N_{DC}=4\times20$ at each loading step. However, estimating $\sigma^l(r')$ values to within one decimeter introduces the cells number $N_c=60\times9\times3$. To solve this underdetermined system, an iterative, least-square algorithm is utilized. Its expression written in a matrix form is expressed as, $$(\sigma^l)^n = (\sigma^l)^{n-1} + [(G^l)^T \cdot (C_{DC}^l)^{-1} \cdot G^l + (C_\sigma^l)^{-1}]^{-1} \cdot (G^l)^T \cdot (C_{DC}^l)^{-1} \cdot [DC^l - G^l \cdot (\sigma^l)^{n-1}] \quad (13)$$

where $$C_{DC}^l = [Nois^l(r_{i,j}) DC^l(r_{i,j})]^2 \delta \quad (14)$$

$$C_\sigma^l = \left(stdm^l \frac{L_0^l}{L_c^l}\right)^2 \exp\left(-\frac{d}{L_c^l}\right) \quad (15)$$

Here the superscript n is the iteration number; and the superscripts T and −1 indicate the transpose and inverse functions of the matrix, respectively. $\sigma^l(r)$ now is written in a column vector of length $N_c$. $G^l$ represents a $N_m \times N_c$ matrix and each row corresponds Sensitivity Kernel results of a source-receiver pair.

In Eq. (11), $C^l_{DC}$ describes the correlations and errors on the decorrelation ($DC^l_{ij}$) calculated from measurement data. $Nois^l(r_{i,j})$ indicates the relative fluctuations (i.e., noise levels) of diffuse wave signal $<E^l(r_{i,j}, t)>$ measurements. Since the measurements collected with each source-receiver pair can be treated as an independent event, $C^l_{DC}$ then becomes a diagonal matrix and $\delta$ here is Kronecker symbol. In addition, $C^l_\sigma$ is a covariance matrix defining the correlations between the model cells, as well as the correlations of estimated results between two successive iterative steps. In strongly scattering concrete structures, this correlation is assumed to follow an exponential function and it is utilized to reduce the under-determination of Eq. (13). Here, $d=|r-r'|$ is a $N_c \times N_c$ matrix comprised of distances between every two cells over the whole beam. $L_0=(\delta V)^{1/3}$ is the length of the elementary cell. $L^l(r_{i,j})$ called the length of the spatial smoothing is the typical correlation distance between cells, and $stdm^l(r_{i,j})$ is the allowed fluctuation of the model. In general, $L_c$ and stdm are tunable parameters of the inversion algorithms, and they are complex functions related to medium properties and waves. But in strongly scattering media, their values can be determined as constants using L-curve method, and for concrete structures, stdml≈5.6×10−4$\lambda^l$ and $L_c^l$≈16$\lambda^l$ where $\lambda^l$=[$\Sigma_c^l(r_{i,j})$/$f_c$]/$N_{DC}$ denotes the mean values of the central wavelength at the loading step l.

Figure 3:
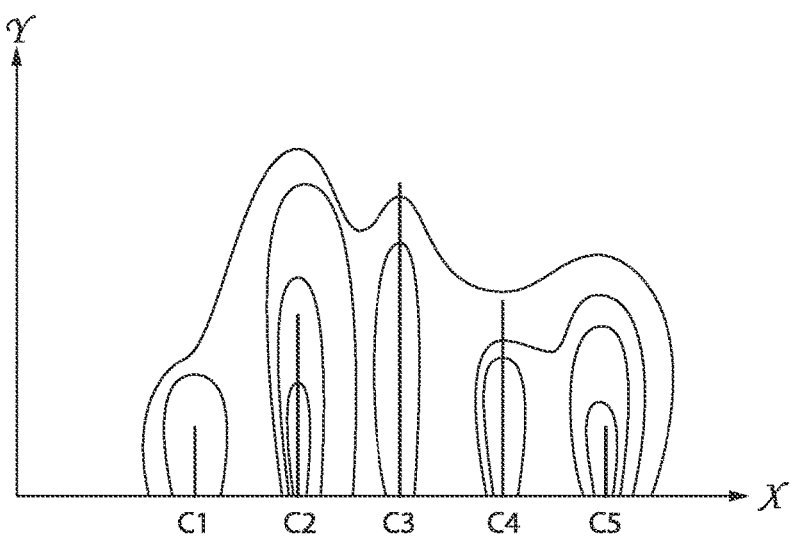
FIG. 3 is an image of the density values correlating with a location (x, y, z=0) of micro-cracks (C1-C5) within the concrete beam.

Applying the Model:

Referring to FIGS. 2 and 3, the $\sigma^l(r)$ values are solved by Eq. (13) above with n=200 iteration calculations as indicated by process block 94, and three-dimensional imaging results comprised of estimation $\sigma^l(r)$ values for each localized position are generated to indicate medium perturbations as indicated by process block 96.

Summary:

The three-dimensional diffuse wave-based images for detecting internal defects may be produced by executing the following steps with reference to the equations above:

1) At each loading step an excitation impulse of each source is repeated 70 times, and the mean diffuse wave <$E^l(r_{i,j}, t)$> results and the wave speed $cl(r_{i,j})$ corresponding to all source-receiver pairs are calculated. The associated standard deviation values of <$E^l(r_{i,j}, t)$> are calculated to estimate the noise levels (i.e., $Nois^l(r_{i,j})$ in Eq. (14) above).

2) The decorrelation coefficients $DC^l(t, \varepsilon, r_{i,j})$ between every two successive loading steps are obtained using Eq. (4) above.

3) The values of the diffusion coefficient $D^l(r_{i,j})$ are estimated from the mean <$E^l(r_{i,j}, t)$> results using nonlinear least-squares or genetic algorithms. Then the concrete beam is discretized into elementary cells of size $\delta V$=3 cm×3 cm×3 cm with cell number $N_c$=199×29×10, and the Sensitivity Kernel $K^l(r_i, r, r_j, t)$ is modeled with Eq. (10) above.

4) The $\sigma^l(r)$ values are solved by Eq. (13) above with n=200 iteration calculations, and three-dimensional imaging results comprised of estimation $\sigma^l(r)$ values for each localized position are generated to indicate medium perturbations.

Embodiment 2

Estimating Stress and Strain Changes from Coda Waves
Model Development:

Coda wave interferometry (CWI) is utilized to quantify coda waveform variations by calculating two straightforward parameters, which can further indicate damage and stress conditions in concrete structures. CWI theory is initially developed to evaluate the seismic waves in geophysics, and is defined as $$DC = 1 - \frac{\int_{T_c-T_w}^{T_c+T_w} h[t(1-dv/v)]h_0(t)dt}{\sqrt{\int_{T_c-T_w}^{T_c+T_w}\{h[t(1-dv/v)]\}^2 dt \int_{T_c-T_w}^{T_c+T_w}\{h_0(t)\}^2 dt}} \quad (16)$$

Here, $h_0$ represents a reference diffuse wave and h denotes a diffuse wave to be inspected. $T_c$ is the central time of a time window with $2T_w$ length. dv/v is the relative velocity variations between two diffuse waves and its value is determined by minimizing the decorrelation coefficient (DC) values; or in other word, making the inspected wave best resemble the reference wave. If only stress changes exist in concrete, by varying dv/v values the tension or compression effects between two diffuse waves are removed and DC values should be small; however, defects causing waveform distortion will significantly increase DC values. Thus, DC is able to be used as a priority parameter to indicate defects: the higher the DC value, the larger probability the defects exist.

There are not any specific requirements for time window $T_c$ and $T_w$ selections; i.e., the step of selecting a specific portion of coda waveforms in the initial CWI method are not required. DC and $\varepsilon$ values are directly calculated for each signal excitation-collection period T, and thus the calculations are straightforward and simple. Eq. (16) now in the proposed techniques simplifies to $$DC = 1 - \frac{\int_0^T h[t(1-dv/v)]h_0(t)dt}{\sqrt{\int_0^T \{h[t(1-dv/v)]\}^2 dt \int_0^T \{h_0(t)\}^2 dt}} \quad (17)$$

External force $\sigma$ below serviceability stages will slightly stretch or squeeze the size of concrete materials, which further cause the tension or compression effects (i.e., dv/v value variations) of diffuse waveforms. The deformations of concrete materials are usually represented by strains ($\varepsilon$) that denote the relative and fractional changes of the bulk dimensions. For springs, this stress-strain relationship can be simply expressed using the well-known linear-elasticity Hooker's law. But concrete is a multiple-composite material that exhibits inherent inhomogeneity and heterogeneity; for example, the direction of applied forces is not always the same as the direction of its deformations. Thus, the stress-strain relationship in concrete follows the second-order approximation of nonlinear-elasticity expression $$\sigma_{ij}=c_{ijkl}\varepsilon_{kl}+c_{jiklmn}\varepsilon_{kl}\varepsilon_{mn} \quad i,j,k,l,m,n=1,2,3 \quad (18)$$

where the subscripts i, j, k, l, m, and n denote the coordinate systems to describe stresses ($\sigma$) and strain ($\varepsilon$) tensors.

To further build the $\sigma$-dv/v (stress-waveform tension/compression) relationship, a couple of complicated derivation steps are required. If external stress conducted at a fixed direction, the $\sigma$-dv/v relationship is given by $$\frac{dv_{IJ}}{v_{IJ}} \approx \frac{k_{IJ} \cdot \sigma}{1+k_{IJ} \cdot \sigma} \quad (\text{if } \sigma^0 = 0) \quad (19)$$

Here, like the subscript i, j, k, l, m, and n, the subscripts I and J are used to define the related coordinate systems, where I indicates the wave propagation direction and J denotes the direction of particle displacement. $k_{ij}$ is the nonlinear elasticity coefficient and its value is related to the directions of stress conduction and wave propagation as well as mixture proportion of concrete materials.

The dv/v values calculated in Eq. (17) now can convert to stress values using Eq. (19).

Embodiment 3

Neutral Axis Determination
Model Development:

Coda wave interferometry (CWI) technique is utilized to quantify coda waveform variations and it is defined by $$DC = 1 - \frac{\int_0^T h^R(t)h^I[t(1+\varepsilon)]dt}{\sqrt{\int_0^T [h^R(t)]^2 dt \int_0^T \{h^I[t(1+\varepsilon)]\}^2 dt}} \quad (20)$$

Here, $h^T$ and $h^I$ denotes the reference coda wave and the inspected coda wave, respectively. DC is the cross-decorrelation coefficient of the two coda waves and T is the total propagation time. ε usually called the relative velocity variation, describes coda waveform stretches or compressions caused by medium changes; and its value is calculated by minimizing DC values, i.e., making the inspected coda wave best resemble the reference wave.

For each source-receiver pair the coda waves collected at the 1st loading step (0 kN) during the propagation time T are utilized as the reference waves, i.e., $h_{ij}^I$ (T); and the inspected coda waves at other loading steps $h_{ij}^I$ (T) (l≠1) are compared to the reference waves using the CWI technique (Eq. (20)). If a concrete structure is under elastic serviceability stages, the external loads will only slightly stretch or compress its shapes, and further stretch or compress coda wave without inducing significant waveform distortion. Then by selecting appropriate ε values, the stretch or compression effects between two coda waveforms should be nearly removed and their DC values in general are small. However, when structure deficiencies such as micro-cracks exist, waveform distortions will appear and DC values will significantly increase.

The inspected coda wave $j_{ij}^I(T)$ are compared to the reference wave $h_{ij}^I(T)$ to calculate the associated $\varepsilon_{ij}^I$ values for all available source-receiver pairs at each loading step l. Then the positive and negative $\varepsilon_{ij}^I$ values are able to indicate the compression and tensile effects conducted on the inspected waves, and the neutral axis is located at the position where $\varepsilon_{ij}^I$ values are approximately equal to 0.

Then at each loading step, the heights of the receivers installed at the T-beam side surface, together with their associated $\varepsilon_{ij}^I$ results are utilized to estimate the position of the neutral axis (i.e., $\varepsilon_{ij}^I=0$).

Embodiment 4

Absolute Stress Determination

Model Development:

In large-size strongly heterogeneous media such as concrete, due to multiple scattering behaviors, waves rapidly lose their initial propagation directions and reach diffuse regimes where wave energy transportation in space and time statistically evolve according to the solution of the three-dimensional diffusion equation:

$$f^d(s_i, r_j, t) = \frac{\langle E^d(r_{ij}, t)\rangle}{E_0} = \frac{1}{[4\pi(D_{ij}^d)t]^{3/2}} \exp\left[-\frac{(r_{ij})^2}{4(D_{ij}^d)t} - (\sigma_{ij}^d)t\right] \quad (21)$$

where the index d, i, and j denote the number of load steps, sources, and receivers, respectively. $\langle E^d(r_{ij}, t)\rangle$ is the mean energy value observed at position and propagation time t, and $E_0$ is the initial energy deposited at source position s, at time t=0. $f^d(s_i, r_j, t)$ denotes the probability density function of the diffuse energy transportation for signal sending at source $s_i$ and detected at location $r_j$ at the loading step d. $D_{ij}^d$ and $\sigma_{ij}^d$ are the diffusion and dissipation coefficients at each loading step recovered from waveforms of each source receiver pair, respectively. Based on the diffusion equation, the sensitivity kernel model is derived based on the probability that a wave train starts at source position $s_i$ at time t=0, visits the position r' at time t', and observed at position $r_j$ after propagation time t. It is given as $$K^d(s_i, r', r_j, t) = \frac{|s_i - r'| + |r_j - r'|}{4\pi(D_{ij}^d)|s_i - r'| + |r_j - r'|} \exp\left[\frac{(r_{ij})^2 - (|s_i - r'| + |r_j - r'|)^2}{4(D_{ij}^d)t}\right] \quad (22)$$

On the other hand, coda wave interferometry (CWI) is a technique to quantify the changes between a reference diffuse wave observation $E^R$ and a diffuse wave observation to be inspected $E^I$, and it is defined by $$CC_{ij}^d = \frac{\int_0^t f^d\{t'[1 - dv/v(s_i, r_j)]\}f^{d-1}(t')dt'}{\sqrt{\int_0^t \{f^d\{t'[1 - dv/v(r_{ij})]\}\}^2 dt' \int_0^t \{f^{d-1}(t')\}^2 dt'}} \quad (23)$$

Here, $CC_{ij}^d$ is the cross-correlation coefficient. The stretch factor $dv/v(s_i, r_j)$ is the relative velocity variation between two diffuse waves and its value is determined by maximizing $CC_{ij}^d$ values. $dv/v(s_i, r_j)$ values are able to denote diffuse waveform variations caused by stress changes, and it is usually utilized as an indicator to evaluate global medium changes. Specifically, concrete is treated as an elastic material, so conducted stresses that are below serviceability stages squeeze (or stretch) the size of concrete structures, which further induces the compression (or tensile) effects on the diffuse waveforms.

The relative velocity variation $dv/v(s_i, r_j)$ is the sum of local relative velocity changes at each position $dv/v(r')$ over the whole volume V of the media. Based on the sensitivity kernel probability model, $dv/v(s_i, r_j)$ and $dv/v(r')$ can be related by combining Eqs. (21) and (22) with a few further derivations, and it is written as:

$$dv/v = \int_0^V \frac{K^d(s_i, r', r_j, t)}{t} dv/v(r')dr' \quad (24)$$

Similar to dv/v values that indicate global stress changes, dv/v(r') values are able to denote stress changes at each local position. Estimating dv/v(r') values from the dv/v calculation results is an important step to evaluate interior stress values.

To solve the inverse problem described by Eq. (24), the concrete structure needs to be discretized into elementary cells and Eq. (24) now is expressed as $$dv/v = \sum_1^N \frac{K^d(s_i, r', r_j, t)}{t} dv/v(r')\delta V = \sum_1^N g(s, r', r, t)dv/v(r') \quad (25)$$

where N and δV are the total number and the size of the elementary cell, respectively. g(s, r', r, t)=K(s, r', r, t)×δV/t can be treated as a matrix including weight coefficients for each dv/v(r') unknown variable. For multiple diffuse wave observations collected with a couple of receivers (the dv/v number M>1), Eq. (25) is written in matrix form, $$X = G \times x \quad (26)$$

Here, X is a column (M×1) matrix and each entry corresponds to a dv/v value. x is also a column (N×1) matrix including all the dv/v(r') unknown variables over the whole volume. G is a M×N matrix and each row describes the sensitivity kernel corresponding to an ultrasound wave source-receiver pair. The dv/v(r') values are estimated to within one centimeter, which implies that N=600×87×30. However, there are only 4 sources and 20 receivers placed on the concrete beam; thus, M=4×20 for each loading step. In general N>>M, the unconstraint least-square iterative algorithms are utilized here to solve this underdetermined inversion problem, $$(x^d)^n = (x^d)^{n-1} + \left[(G^d)^T \cdot (C_D^d)^{-1} \cdot G^d + (C_M^d)^{-1}\right]^{-1} \cdot (G^d)^T \cdot (C_D^d)^{-1} \cdot \left[X^d - G^d \cdot (x^d)^{n-1}\right] \quad (27)$$

where the superscript T and −1 stand for matrix transpose and inverse functions, as well as n is the iteration calculation number. Without any prior knowledge of dv/v(r') values, the initial entries in the $x^0$ matrix are all set as zero. C D is utilized to account for the covariance among dv/v results and it is a diagonal M×M matrix since diffuse wave measurements are considered to be independent events. Each non-zero entry in $C_D$ is given by $$C_D = \frac{1 - (CC_{ij}^d)^2}{CC_{ij}^d} \frac{6\sqrt{\pi/2}}{\Delta f(2\pi f_C)t^2} \quad (28)$$

where $\Delta f$ and $f_c$ are the frequency bandwidth and center frequency of the diffuse wave detection. $CC^d_{ij}$ is the correlation coefficient defined by Eq. (23) and t is the propagation time. $C_M$ is a N×N covariance matrix utilized to reduce the under-determination of Eq. (27) is written as where $$C_M = \left(std \frac{L_0}{L_C}\right)^2 \exp\left(-\frac{d}{L_C}\right) \quad (29)$$

where $$std = 5.6 \times 10^{-4} \lambda_0 \text{ and } L_C \approx 16 \lambda_0 \quad (30)$$

d=|r−r'| is a N×N matrix comprised of distances between every two elementary cells, $L_0$ is the length of the elementary cell, and $\lambda_0$ denotes the central wavelength. $L_c$ and std are the length of the spatial smoothing length and allowed model fluctuation, respectively; and these two tunable parameters define the correlations of the dv/v(r') estimation values between elementary cells and iterative steps. In general, $L_c$ and std are complex functions related to medium and wave properties. But for concrete structures with strongly scattering inherent, the correlation in $C_M$ is assumed to follow an exponential function and the values of $L_c$ and std can be calculated using Eq. (30) derived from the L-curve method.

Concrete is a complex, multi-composite material that exhibits high nonlinearity, hysteresis and discrete memory. The second-order approximation is usually considered to describe the stress-strain relation, and it is defined by Eq. (31)

$$\sigma_{ij} = c_{ijkl}\varepsilon_{kl} + \frac{1}{2}c_{ijklmn}\varepsilon_{kl}\varepsilon_{mn} \quad (31)$$

where σ and ε are stress and strain tensors respectively; $c_{ijkl}$ is the second-order elastic constants that can be defined by Lamé constants λ and μ; $c_{ijklmn}$ is the third-order elastic constants that are defined by Murnaghan constants l, m and n.

Based on the nonlinear-behavior laws, the theoretical expressions between stress and acoustic-wave velocities for isotropic media are expressed as $$\rho_0 V_{11}^2 = \lambda + 2\mu + \sigma[4(\lambda + 2\mu) + 2(\mu + 2m) + \nu\mu(1 + 2l/\lambda)] \quad (32a)$$

$$\rho_0 V_{12}^2 = \rho_0 V_{13}^2 = \mu + \sigma\left[4\mu + \nu\left(\frac{x}{2}\right) + m(1 - 2\nu)\right] \quad (32b)$$

$$\rho_0 V_{22}^2 = \lambda + 2\mu + \sigma[2l(1 - 2\nu) - 4\nu(m + \lambda + 2\mu)] \quad (32c)$$

$$\rho_0 V_{21}^2 = \rho_0 V_{31}^2 = \mu + \sigma[(\lambda + 2\mu + m)(1 - 2\nu) + 1/2n] \quad (32d)$$

$$\rho_0 V_{23}^2 = \rho_0 V_{32}^2 = \mu + \sigma[(\lambda + m)(1 - 2\nu) - 6\nu\mu - 1/2n] \quad (32e)$$

Here, the first subscripts of the V's (1, 2 and 3) indicate the propagation direction of the wave, and the second subscripts 1, 2 and 3 denote the direction of particle displacement, respectively. σ is the uniaxial compressive stress and ν is poison's ratio. $\rho_0$ is the density of the media under the undeformed state.

When relative wave velocity changes are small, their values can be derived from Eq. (32).

$$\frac{dV_{11}/V_{11}^0}{d\sigma} = 2 + \frac{\mu + 2m + \nu\mu(1 + 2l/\lambda)}{\lambda + 2\mu} \quad (33a)$$

$$\frac{dV_{12}/V_{12}^0}{d\sigma} = 2 + \frac{\nu n}{4\mu} + \frac{m}{2(\lambda + \mu)} \quad (33b)$$

$$\frac{dV_{22}/V_{22}^0}{d\sigma} = -2\nu\left(1 + \frac{m - \mu l/\lambda}{\lambda + 2\mu}\right) \quad (33c)$$

$$\frac{dV_{21}/V_{21}^0}{d\sigma} = \frac{\lambda + 2\mu + m}{2(\lambda + \mu)} + \nu n/4\mu \quad (33d)$$

$$\frac{dV_{23}/V_{23}^0}{d\sigma} = \frac{m - 2\lambda}{2(\lambda + \mu)} - \frac{n}{4\mu} \quad (33e)$$

where the superscript 0 of $V_{ij}$ stands for the wave velocity when the stress is zero.

Eq. (33) indicates that the relative velocity change $dV_{ij}/V^0_{ij}$ is approximately linearly varied stress change dσ. In general, the observed velocity was related to direct waves. However, direct waves are only effective when the wave particle displacement (polarization) is parallel to the applied stress direction, which implies that loading directions and structure shapes must be known prior. In addition, Eq. (33) could only be effective to detect stress changes in the order of 100 MPa with the measured direct wave velocity change $dV_{ij}/V^0_{ij}$, according to the previous experimental study on third-order elastic constants determination. Recent studies show that coda waves that arrive later in the waveform are much more sensitive to weak stress changes. The coda waves experiencing multiple-scattering in a large volume, carry more interior information of the media. Coda waves can be evaluated using the coda wave interferometry technique that is capable of detecting small stress changes in the order of 1 MPa.

Eq. (33) is rewritten in a general form:

$$\frac{dV_{ij}/V_{ij}^0}{d\sigma} = K_{ij} \quad (34)$$

where $K_{ij}$ contains the Lamé's constants and Murnaghan constants. For the application of in-situ stress measurement in a structural member, $V^0_{ij}$ is usually unknown and hard to measure. Hence, it is convenient to transfer Eq. (33) to another general form expressed as:

$$\frac{dV_{ij}}{V_{ij}} = \frac{K_{ij}d\sigma}{1+K_{ij}d\sigma} \quad (35)$$

Note, $d\sigma$ in Eq. (32)-(35) is the stress change from zero stress state, so $d\sigma$ denotes the absolute stress as well. Hence, given the measured $K_{ij}$ from a reference specimen and relative velocity change $$\frac{dV_{ij}}{V_{ij}}$$

between the two loading state of the structure, both the stress change and the absolute stress in the structure could be evaluated.

Figure 4:
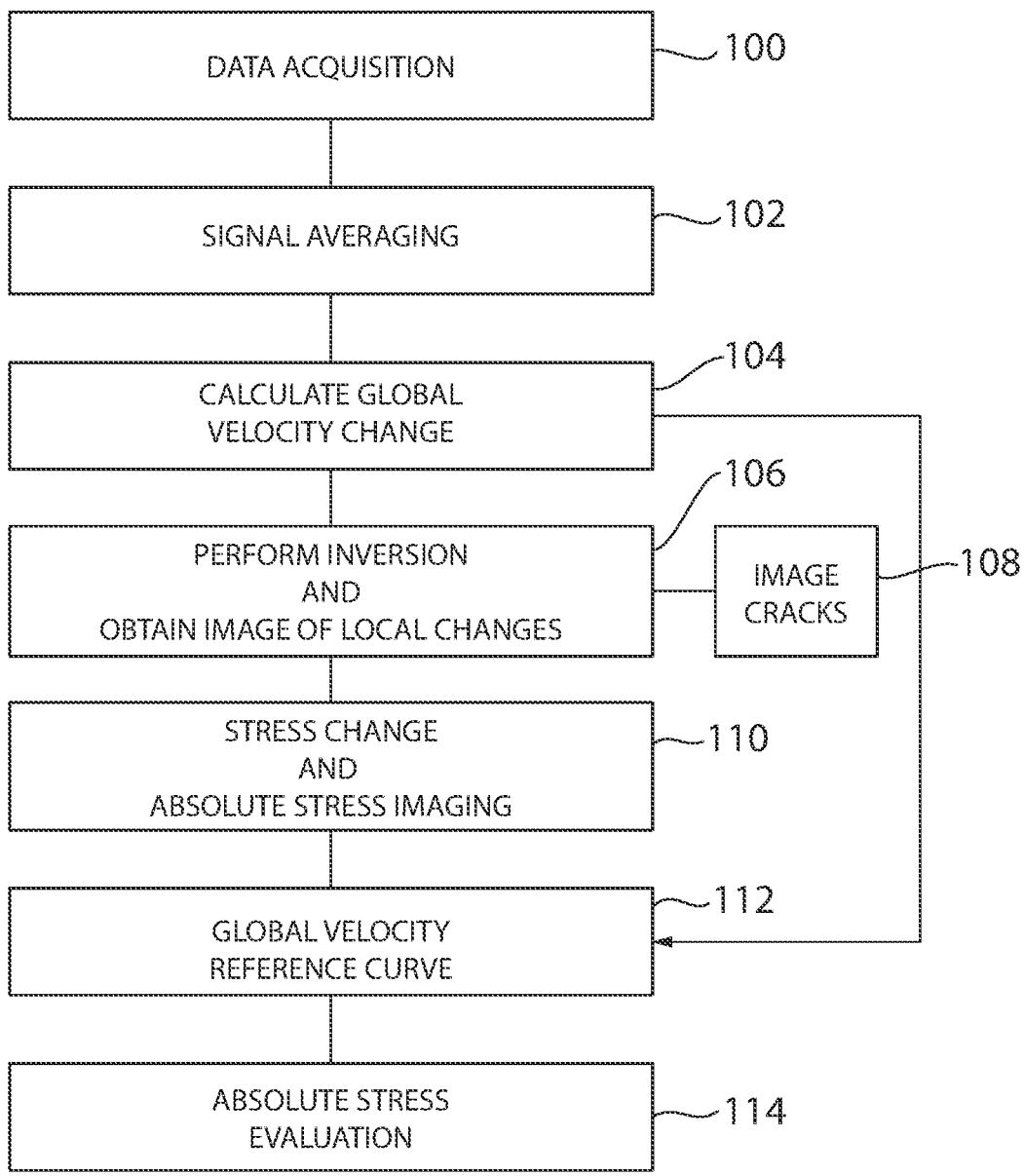
FIG. 4 is a flow chart showing a method of detecting absolute stress within concrete.

Applying the Model:

Referring to FIGS. 1 and 4, the system is similar to the one described with respect to FIG. 1, however it may be preferable to install the transmitters 40 along the roughly estimated neutral axis on the vertical web of the beam based on fundamental structural analysis. The receivers 50 then should be sparsely placed both in tension zone and compression zone due to stress changes. For pre-stressed concrete beam 10, the neutral axis is referring to the zero stress change axis, not the zero absolute stress location.

The receivers 50 should be placed far enough from the zero stress change axis to avoid being influenced by the loading effects on the other side of the zero stress change axis. There is a trade-off between minimizing the loading effects from the other side of zero stress change axis and receiving signals strong enough to be captured.

In some circumstances, the stresses at some key points are focused and the zero stress change axis location does not matter. In this case, it is suggested that all the transmitters 40 should be placed on the top or bottom plane that is experiencing the largest and relatively uniform stress.

For large size structures, it is suggested that narrow band pulse signals are at a central frequency of 150 kHz and broad band receivers have frequencies of 60 kHz to 400 kHz. To generate the dv/v(r') image representing the local change distribution (stress, crack or combined stress and crack induced), one of the sensors will be connected to the pulse generator acting as a source, and all the other sensors synchronously receive signals through the multi-channel data acquisition system. Some of sensors act as sources alternatively to obtain more dv/v measurements from source receiver pairs. The more dv/v measurements provided, the better converged and faster generated images would be.

At least 50 waveform signals should be collected as indicated by process block 100 and averaged to reduce the signal to noise ratio as indicated by process block 102. Then the algorithm expressed in Eq. (23) is applied to obtain the global velocity change dv/v for the tested beam at each receiver location as indicated by process block 104.

Absolute Stress Evaluation at the Locations of Receivers (Fast Procedure)

First, a small specimen with a standard size composed of the same material as the full size beam is put to a loading test to mimic the loading history and state of the full size beam. The dv/v to stress curve of the specimen that best represents the stress state of the full size beam is selected to compare with the dv/v to stress curve of the beam as indicated by process block 112. Then the initial stress at the examined point could be obtained from structural analysis based on design plans. Given a measured dv/v caused by an applied loading together with the estimated initial stress, the final absolute stress could be evaluated on the reference curve as indicated by process block 114.

Imaging Absolution Stress and Stress Change Distribution (Involving the Inversion Algorithm that has a Longer Processing Time)

Similar to above, the absolute stress distribution in the full size beam could also be imaged by comparing the local dv/v(r') values in the discretized cells of the beam with the dv/v(r') value in the cube with the same sized discretized cells. The three-dimensional images comprised of dv/v(r') and absolute stress $P_{beam}$(r') show the absolute stress distribution in the bulk of the concrete beam as indicated by process block 106. In addition, local dv/v(r') itself indicates the stress change in the cross section that is least affected by cracking perturbation, so the image of dv/v(r') could be used to denote the stress change distribution at that cross section as indicated by process block 110.

Imaging the Cracks

Theoretically, dv/v(r') indicates the small stress change in the bulk of the concrete beam. However, with the cracking further developed, dv/v(r') values also include the media change caused by cracking that is usually considered as extra scatters. Hence, the cracking images may be generated first as indicated by process block 108, then the cross section that is least affected by the cracking could be located and used to image the stress.

Summary:

The estimation and imaging of stress changes in absolute stress values in three-dimensional models using ultrasound diffusion and nonlinear acoustoelasticity theories may be produced by executing the following steps with reference to the equations above:

1) Transducers are placed sparsely at the beam's surface to collect diffuse ultrasound waves, and their relative wave velocity changes ($dv/v_{beam}$) caused by different external loads are calculated using coda wave interferometry techniques.

2) $dv/v_{beam}$ (r') values at each local position of the beam are determined by the application of inverse algorithms to the sensitivity kernel expression derived from the diffusion equation.

3) A loading test is conducted on a concrete cube and its dv/v cube values varied with the associated stress values are set as a reference curve.

4) The absolute stress values $P_{beam}$ (r') at each local position of the concrete beam are estimated using its dv/v beam values through the reference curve and acoustoelasticity theory.

5) The absolute stress distribution in the full size beam are imaged by comparing the local dv/v(r') values in the discretized cells of the beam with the dv/v(r') value in the cube with the same sized discretized cells.

6) Three-dimensional images comprised of dv/v(r') and $P_{beam}$ (r') show features that denote stress change and absolute stress values in the bulk of the concrete beam.

The present invention described above provides the following advantages:

1) Large Detection Volume: the proposed technique can detect large volumes of structures including internal medium more than just the concrete located in a direct line between the transmitting and receiving transducers.

2) High Sensitivity and Accuracy: the proposed technique can detect micro-defects and weak stress changes in concrete with a high degree of accuracy.

3) Easy to Setup and Operate: the proposed technique only requires the signal excitation-collection-analysis steps using fixed sensor locations, and two straightforward parameters are calculated to evaluate damages and stress conditions in large-size concrete structures in real-time.

4) Ability to monitor defects and stress simultaneously: in the proposed technique, detecting the defect is set to be a priority task. If no defects exist, the stress conditions can also be monitored, which is worked as an early warning system.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. A testing system for concrete structures comprising:
a load sensor positionable to measure a load on the concrete structure to distinguish between at least two different load values;
a plurality of transmitters positionable on the structure and configured to independently transmit acoustic excitation waves into the structure;
a plurality of receivers positioned positionable on the structure and configured to receive diffuse waves of the excitation waves from the plurality of transmitters; and
an electronic computer executing a program stored in a non-transitory medium to:
receive the diffuse waves from the plurality of receivers;
calculate a decorrelation coefficient based on the diffuse waves and a wave speed of the diffuse waves for at least two different load values;
calculate a sensitivity kernel based on the diffuse waves; and
apply an inversion algorithm to estimate a distribution density based on the decorrelation coefficient and the sensitivity kernel and indicating a presence of defects within the concrete structure.

2. The system of claim 1 wherein the defects are cracks.

3. The system of claim 1 wherein the electronic computer further executes the program stored in the non-transitory medium to:
receive a plurality of diffuse waves at multiple times at each load value; and
calculate a mean diffuse wave from the plurality of diffuse wave.

4. The system of claim 1 wherein the electronic computer further executes the program stored in the non-transitory medium to:
output an image of the distribution density as a function of beam location.

5. The system of claim 1 wherein the electronic computer further executes the program stored in the non-transitory medium to:
calculate at least one depth of the defects within the beam.

6. The system of claim 1 wherein the excitation waves are transmitted at a frequency between 60 kHz and 400 kHz.

7. The system of claim 6 wherein the excitation waves are transmitted at a frequency between 100 kHz and 200 kHz.

8. The system of claim 7 wherein the excitation waves are transmitted at a frequency of 150 kHz.

9. The system of claim 1 wherein the excitation waves are driven by a voltage ranging between 3 V to 9 V.

10. The system of claim 9 wherein the excitation waves are driven by a voltage centered on 5.7 V.

11. The system of claim 1 wherein the load sensor is a strain gauge.

12. The system of claim 1 wherein the load sensor is a load jack applying a known load.

13. The system of claim 1 wherein the plurality of transmitters are positioned along a horizontal centerline of the beam, the centerline extending along an axis of the beam and centered between a width of the beam.

14. The system of claim 13 wherein the plurality of receivers are positioned along the axis of the beam and flank the centerline of the beam to surround the plurality of the transmitters.

15. The system of claim 14 wherein a second plurality of receivers are positioned on a perpendicular surface to the plurality of receivers.

16. The system of claim 1 wherein the decorrelation coefficient is estimated using nonlinear least-squares or genetic algorithms.

17. The system of claim 16 wherein the decorrelation coefficient is calculated using:

$$DC^l(t, \varepsilon, r_{i,j}) = 1 - \frac{\int_0^t \langle E^l[r_{i,j}, t'(1-\varepsilon)]\rangle\langle E^{l-1}[r_{i,j}, t']\rangle dt'}{\sqrt{\int_0^t \langle E^l[r_{i,j}, t'(1-\varepsilon)]\rangle^2 dt' \int_0^t \langle E^{l-1}(r_{i,j}, t')\rangle^2 dt'}}$$

where t indicates a wave propagation time, $r_i$, r and $r_j$ represent central positions of the associated elementary cells of the beam, l denotes a loading step, E represents a reference diffuse wave, $\varepsilon$ is a relative velocity variations between two diffuse waves.

18. The system of claim 1 wherein the sensitivity kernel is calculated using:

$$K^l(r_i, r, r_j, t) = \frac{|r_i - r| + |r_j - r|}{4\pi D^l(r_{i,j})|r_i - r||r_j - r|} \exp\left[\frac{(r_{ij})^2 - (|r_i - r| + |r_j - r|)^2}{4D^l(r_{i,j})t}\right]$$

where t indicates a wave propagation time, $r_i$, r and $r_j$ represent central positions of the associated elementary cells of the beam, D denotes a diffusion coefficient.

\* \* \* \* \*